United States Patent [19]

Zaiger

[11] Patent Number: Plant 5,623

[45] Date of Patent: Jan. 7, 1986

[54] NECTARINE TREE (TASTY-GOLD)

[76] Inventor: Chris F. Zaiger, 537 Rosemore Ave., Modesto, Calif. 95351

[21] Appl. No.: 599,671

[22] Filed: Apr. 12, 1984

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

A new and distinct variety of nectarine tree which is of large size, vigorous upright growth and the tree being a productive, regular bearer of large, yellow flesh, freestone fruit with a high degree of red skin color. The fruit is further characterized by its ability to hold firm on the tree after maturity (shipping ripe) for a period of 10 to 14 days; the maturity period being 3 to 4 days before Fibebrite Nectarine (non-patented).

1 Drawing Figure

ORIGIN OF THE VARIETY

The new variety of nectarine tree was originated by me in my experimental orchard near Modesto, Calif. as a second generation seedling of a cross between Rub Gold Nectarine (U.S. Plant Pat. No. 3,101) and a peach seedling that originated from a cross between Early Sun Grand Nectarine (U.S. Plant Pat. No. 1,420) and Royal Gold Peach (U.S. Plant Pat. No. 2,663).

ASEXUAL REPRODUCTION OF THE VARIETY

The present variety was asexually reproduced by budding as performed in my experimental orchard at Modesto, Calif., shows that said characteristics come true to form and are established and transmitted through succeeding propagations.

SUMMARY OF THE VARIETY

The present discovery relates to a new and distinct variety of nectarine tree; its novelty consists of the following unique features which are outstanding in the new variety;

1. The large size of the fruit.
2. Coloring of the fruit two to three weeks before maturity.
3. The ability of the fruit to stay firm on the tree 10 to 14 days after maturity (shipping ripe).
4. The excellent shipping and storage ability of the fruit.
5. Having fruit with a high degree of desirable red skin color.
6. The excellent eating quality of the fruit.

DESCRIPTION OF THE PHOTOGRAPH

The accompanying photographs show typical specimens of the fruit and foliage of my new nectarine variety. The upper and lower surface of the foliage being illustrated, the exterior and a fruit being divided on its suture plane to reveal flesh coloration and showing a stone remaining in place. The photographs were taken shortly after being picked (shipping ripe) and the colors are as nearly true as reasonably possible in color representations of this type.

DESCRIPTION OF THE VARIETY

The following is a detailed description of the foliage and fruit of my new nectarine variety, as based upon observations of specimens grown in Modesto, Calif., with color terminology (except those in common terms)

in accordance with Reinhold Color Atlas by A. Kornerup and J. H. Wanscher.

Tree:
- *Size.*—Large.
- *Vigor.*—Vigorous.
- *Form.*—Upright.
- *Shape.*—Usually pruned to vase shape.
- *Production.*—Productive.
- *Bearing.*—Regular.

Trunk:
- *Size.*—Medium to stocky.
- *Texture.*—Shaggy.

Branches:
- *Size.*—Medium stocky.
- *Texture.*—Smooth to medium rough.
- *Lenticels.*—Medium size. Medium number.
- *Color.*—New growth — Reddish brown. Old growth — Brown to grayish brown.

Leaves:
- *Size.*—Large. Average length — $7\frac{3}{8}''$. Average width — $\frac{3}{4}''$.
- *Texture.*—Smooth.
- *Petiole.*—Medium length.
- *Form.*—Lanceolate.Acutely pointed.
- *Margin.*—Crenate.
- *Glands.*—Large — reniform. Number varies 2 to 6. Average number 4.
- *Color.*—Upper surface — Deep green (28-F-7) to (28-F-8). Lower surface — Grayish green (28-D-5) to (28-E-5).

Flower buds:
- *Size.*—Medium.
- *Length.*—Medium.

Flower:
- *Size.*—Large — showy.
- *Pollen.*—Present.
- *Color.*—Pink.
- *Blooming period.*—Feb. 27, 1980 to Mar. 9, 1980.

Fruit:
- *Maturity when described.*—Hard ripe.
- *Date of first picking.*—July 3, 1980.
- *Date of last picking.*—July 10, 1980.
- *Size.*—Large. Average diameter axially — $2\frac{5}{8}''$ to $3\frac{1}{4}''$. Average transversely in suture plane — 2 7/16" to 3".
- *Form.*—Globose — Slightly flattened at stem end.
- *Suture.*—Shallow — extends from base to apex.

*Cavity.*—Rounded. Average depth — 7/16" to ½". Average breadth — 1" to 1⅛".

*Apex.*—Varies from retuse to very slight pistil point.

Flesh

*Color.*—Dark yellow (4-A-8) to cadmium orange (5-A-7). Area near stone and surface of pit cavity red (9-B-8) with yellow fibers.

*Juice.*—Moderate.

*Texture.*—Firm, meaty.

*Ripens.*—Even.

*Flavor.*—Sub-acid to mild.

*Aroma.*—Very little.

*Eating quality.*—Excellent.

Skin:

*Thickness.*—Medium.

*Texture.*—Tough — Tenacious to flesh.

*Tendency to crack.*—None.

*Down.*—Wanting.

*Color.*—Yellow ground color — (4-A-7) to (4-A-8) almost entirely overspread with red (9-A-8) to (10-A-8).

Stone:

*Type.*—Freestone.

*Size.*—Medium to large. Average length — 1 ⅝". Average width — 1 1/16". Average thickness — ⅝".

*Form.*—Obovate.

*Base.*—Oblique.

*Apex.*—Acuminate.

*Sides.*—Nearly equal.

*Surface.*—Irregularly furrowed toward apex, pitted toward base.

*Color.*—Brown (7-E-7) to (7-E-8).

*Tendency to split.*—Very slight.

Use: Dessert. Market, local and long distance shipping.

Keeping quality: Excellent.

Shipping quality: Excellent.

The nectarine tree and its fruit herein described may vary in slight detail due to climatic and soil conditions under which the variety may be grown. The description is that of the variety produced under ecological conditions prevailing at Modesto, Calif.

I claim:

1. A new and distinct variety of nectarine tree, as illustrated and described, which is a regular and productive bearer of large, yellow flesh, freestone fruit with excellent eating quality and maturing 3 to 4 days earlier than Firebrite Nectarine (non-patent); the fruit is further characterized by coloring two to three weeks before maturity, having excellent shipping and storage quality and having the ability to hold firm on the tree 10 to 14 days after maturity (shipping ripe).

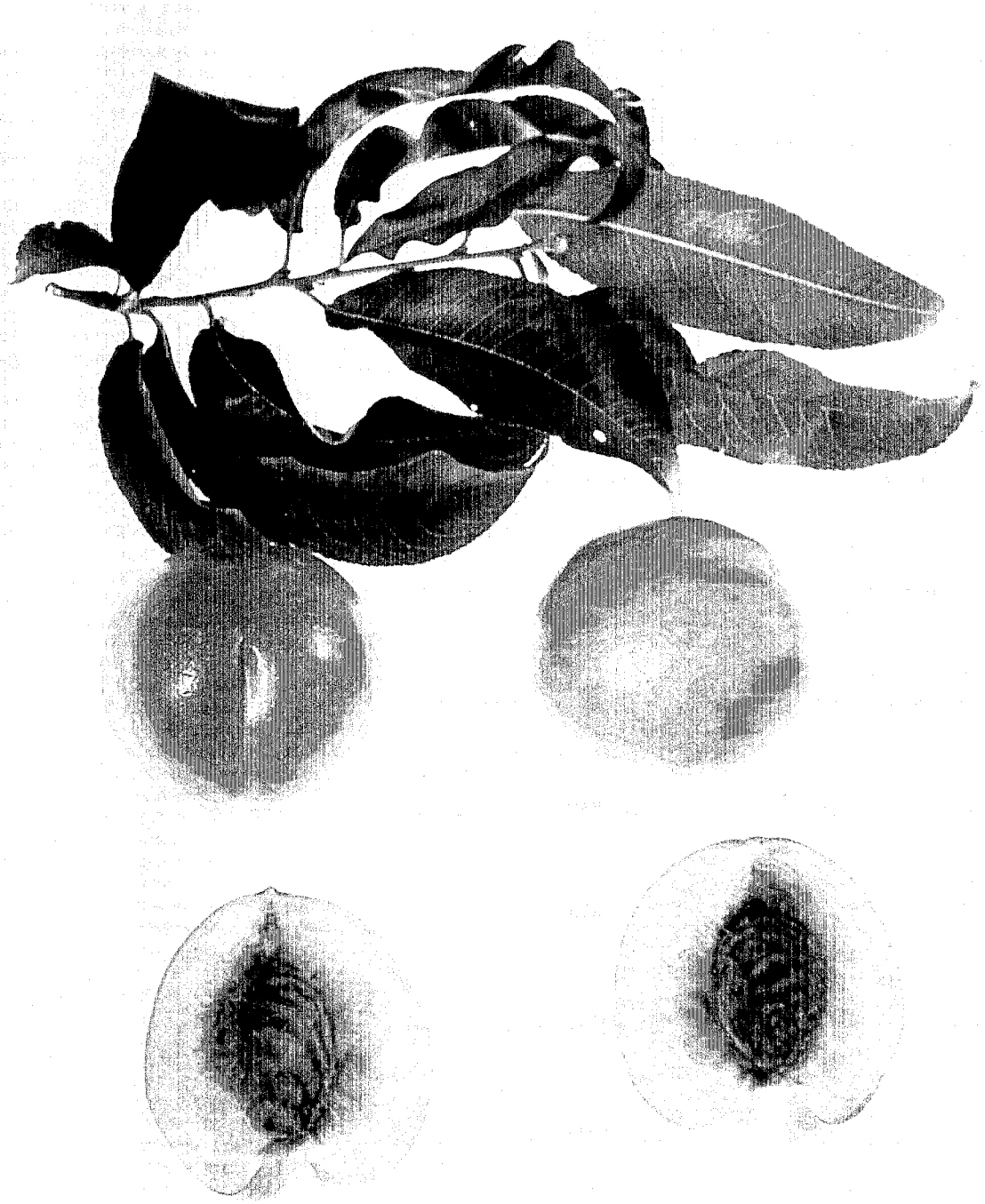

* * * * *